(12) United States Patent
Jung et al.

(10) Patent No.: US 6,251,057 B1
(45) Date of Patent: Jun. 26, 2001

(54) DEHYDROHALOGENATIVE COUPLING REACTION OF ORGANIC HALIDES WITH SILANES

(75) Inventors: Il Nam Jung, Seoul; Bok Ryul Yoo, Koyang; Joon Soo Han, Seoul; Seung-Hyun Kang, Seoul; Yeon Seok Cho, Seoul, all of (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/543,546

(22) Filed: Apr. 5, 2000

(30) Foreign Application Priority Data

Apr. 13, 1999 (KR) .................................................. 99-13006
Mar. 15, 2000 (KR) .................................................. 00-13090

(51) Int. Cl.$^7$ ...................................................... C07F 7/08
(52) U.S. Cl. ...................................................... 572/481
(58) Field of Search .............................................. 556/481

(56) References Cited

U.S. PATENT DOCUMENTS

| | | | | |
|---|---|---|---|---|
| 3,699,143 | * | 10/1972 | Benkeser et al. | ..................... 556/481 |
| 4,985,580 | * | 1/1991 | Chadwick et al. | ..................... 556/481 |
| 5,118,829 | * | 6/1992 | Gohndrone | ............................ 556/481 |
| 5,508,460 | * | 4/1996 | Berry et al. | ........................... 556/481 |

OTHER PUBLICATIONS

N. Furuya, et al. The Condensation Reaction of Trichlorosilane with Allylic Chlorides Catalyzed by Copper Salts in the Presence of a Tertiary Amine; Journal of Organometallic Chemistry, 96 (1975) C1–C3.

Robert J.P. Corriu, et al., Synthesis and reactivity of bis(triethoxysilyl)methane, tris(triethoxysilyl)methane and some derivatives[1]; Journal of Organometallic Chemistry 562 (1988) 79–88.

R.A. Benkeser, et al, Silylation of Organic Halides. A New Method of Forming the Carbon–Silicon Bond; Journal of the American Chemical Society, 91:13, pp. 3666–3667, Jun. 18, 1969.

R.A. Benkeser, et al, Trichlorosilane–Tertiary Amine Combinations as Reducing agents for Polyhalo Compounds. Potential Analogies with Phosphorus Chemistry; Journal of the American Chemical Society, 90:10, Sep. 11, 1968.

* cited by examiner

Primary Examiner—Paul F. Shaver
(74) Attorney, Agent, or Firm—Oblon, Spivak, McClelland, Maier & Neustadt, P.C.

(57) ABSTRACT

The present invention relates to methods for making the compounds of formula I which is a dehydrohalogenative coupling of hydrochlorosilanes of formula II with organic halides of formula III in the presence of a Lewis base catalyst.

$$R^3CH_2SiR^1Cl_2 \qquad (I)$$

$$HSiR^1Cl_2 \qquad (II)$$

$$R^2CH_2X \qquad (III)$$

In formulas I and II, $R^1$ represents a hydrogen, chloro, or methyl; in formula III, X represents a chloro or bromo; in formula III, $R^2$ can be selected from the group consisting of a $C_{1-17}$ alkyl, a $C_{1-10}$ fluorinated alkyl with partial or full fluorination, a $C_{1-5}$ alkenyl groups, a silyl group containing alkyls, $(CH_2)_nSiMe_{3-m}Cl_m$ wherein n is 0 to 2 and m is 0 to 3, aromatic groups, $Ar(R')_1$ wherein Ar is $C_{6-14}$ aromatic hydrocarbon, R' is a $C_{1-4}$ alkyl, halogen, alkoxy, or vinyl, and q is 0 to 5, a haloalkyl group, $(CH_2)_pX$ wherein p is 1 to 9 and X is a chloro or bromo; or an aromatic hydrocarbon, Ar $CH_2X$ wherein Ar is $C_{6-14}$ aromatic hydrocarbon and X is a chloro or bromo. in formula I, $R^3$ is the same as $R^2$ in formula III and further, $R^3$ can also be $(CH_2)_pSiR^1Cl_2$ or $ArCH_2SiR^1Cl_2$ when $R^2$ in formula III is $(CH_2)_pX$ or $ArCH_2X$, because of the coupling reaction of X with the compound of formula II.

17 Claims, No Drawings

DEHYDROHALOGENATIVE COUPLING REACTION OF ORGANIC HALIDES WITH SILANES

BACKGROUND OF THE INVENTION

1. Field of the Invention

The present invention relates to processes for making the compounds of formula I which comprise a dehydrohalogenative coupling of hydrochlorosilanes of formula II with organic halides of formula III in the presence of Lewis base catalyst.

$$R^3CH_2SiR^1Cl_2 \quad (I)$$

$$HSiR^1Cl_2 \quad (II)$$

$$R^2CH_2X \quad (III)$$

In formulas I and II, $R^1$ represents a hydrogen, chloro, or methyl; in formula III, X represents a chloro or bromo; in formula III, $R^2$ can be selected from the group consisting of a $C_{1-17}$alkyl, a $C_{1-10}$ fluorinated alkyl with partial or full fluorination, a $C_{1-5}$ alkenyl groups, a silyl group containing alkyls, $(CH_2)_nSiMe_{3-m}Cl_m$ wherein n is 0 to 2 and m is 0 to 3, aromatic groups, $Ar(R')_q$ wherein Ar is $C_{6-14}$ aromatic hydrocarbon, R' is a $C_{1-4}$ alkyl, halogen, alkoxy, or vinyl, and q is 0 to 5, a haloalkyl group, $(CH_2)_pX$ wherein p is 1 to 9 and X is a chloro or bromo; or an aromatic hydrocarbon $ArCH_2X$ wherein Ar is $C_{6-14}$ aromatic hydrocarbon and X is a chloro or bromo. in formula I, $R^3$ is the same as $R^2$ in formula III and further, $R^3$ can also be $(CH_2)_pSiR^1Cl_2$ or $ArCH_2SiR^1Cl_2$ when $R^2$ in formula III is $(CH_2)_pX$ or $ArCH_2X$, because of the coupling reaction of X with the compound of formula II.

2. Description of the Prior Art

In 1968, Benkeser and Smith reported the reduction of carbon tetrachloride to chloroform by using a 1:1 mixture of trichlorosilane and tertiary amine as reducing agents (Benkeser, R. A.; Smith, W. E. *J. Am. Chem. Soc.* 1968, 90, 5307). They proposed that the amine-catalyzed reduction of carbon tetrachloride to chloroform proceeded via the formation of (trichloromethyl)trichlorosilane by the dehydrochlorinative coupling reaction between the carbon tetrachloride and trichlorosilane, and subsequent cleavage of the carbon-silicon bonded species by ammonium chloride to give chloroform and tetrachlorosilane. In 1969, Benkeser and co-workers also reported that benzyl chloride and benzyl chlorides could be silylated with trichlorosilane-tertiary amine 1:1 mixture to give the corresponding trichlorosilyl substituted products by the dehydrochlorinative coupling reaction (Benkeser, R. A., Gaul, J. M.; Smith, W. E. *J. Am. Chem. Soc.* 1969, 91, 3666).

In 1975, Furuya and Sukawa reported allytrichlorosilane could be prepared in high yield by a coupling reaction of allyl chloride with a 1:1 mixture of trichlorosilane and tertiary amine in the presence of copper chloride as a catalyst (Furuya, N.; Sukawa, T. *J. Organometal. Chem.* 1975, 96, C1).

Recently, Corriu and co-workers reported that the reaction of chloroform with trichlorosilane in the presence of excess tributylamine gave bis(trichlorosily)methane and tris (trichlorosilyl)methane (Corriu, R. J. P.; Granier, M.: Lanneau, G. F. *J. Organometal. Chem.* 1998, 562, 79). These reports suggest that a chloroalkyl group containing organic compounds and organosilanes having Si-H bonds could undergo the dehydrochlorinative coupling reaction with trichlorosilane in the presence of an organic base.

The dehydrochlorinative coupling reaction is a novel method of forming silicon-carbon bonds useful for the synthesis of organosilicon compounds. Although the dehydrochlorinative coupling reaction of activated alkyl chlorides such as benzyl chloride or allyl chloride have been reported, the coupling reaction of unactivated alkyl chlorides with trichlorosilane has never been reported. In the previously reports, tertiary amine was used in excess, more than the stoichiometric amount respect to alkyl chloride. The tertiary amine used is a hydrogen chloride scavenger rather than a catalyst. Since the ammonium salt obtained from the tertiary amine and hydrogen chloride have to be neutralized to recycle the amine, it would be too costly to be utilized on an industry scale. It is necessary to find a way to reduce the usage of the amine or find another effective catalyst to apply the coupling reaction for industrial purposes.

The present inventors have discovered that a coupling reaction of alkyl halides and hydrochlorosilanes in the presence of various tertiary amines or tertiary phosphines as a catalyst proceeded to give the corresponding coupled products by liberating hydrogen halide as a gas. The dehydrohalogenative coupling reaction can be applied to not only the activated alkyl halides such as benzyl chloride or allyl chloride, but also to the unactivated alkyl halides such as n-alkylhexyl chloride or haloalkyl substituted organosilicon compound. Suitable amine catalysts include, but are not limited to triethylamine, tri-n-propylamine, tri-n-butylamine, N,N,N',N'-tetramethylethylenediamine, pyridine, N,N-dimethyltoluidine, N-alkylpyrrolidine. Suitable phosphine catalysts include, but are not limited to tributylphosphine, triethylphosphine, tricyclohexylphosphine, triphenylphosphine, bis (diphenylphosphine)methane, 1,2-bis(diphenylphosphine) ethane, and phosphine coordinated transition metallic compounds such as tetrakis(triphenylphosphine)palladium, tris (triphenylphosphine)rhodium chloride, or tetrakis (triphenylphosphine)platinum.

SUMMARY OF THE INVENTION

The present invention relates to processes for making compounds of formula I which comprises a dehydrohalogenative coupling between hydrochlorosilanes of formula II and organic halides of formula III in the presence of a Lewis base catalyst.

The reaction can be illustrated as follows:

$$HSiR^1Cl_2 + R^2CH_2X \longrightarrow R^3CH_2SiR^1Cl_2 + HX$$
$$(II) \qquad (III) \qquad \qquad (I)$$

In formulas I and II, $R^1$ represents a hydrogen, chloro, or methyl; in formula III, X represents a chloro or bromo; in formula III, $R^2$ can be selected from the group consisting of a $C_{1-17}$ alkyl, a $C_{1-10}$ fluorinated alkyl with partial or full fluorination, a $C_{1-5}$ alkenyl groups, a silyl group containing alkyls, $(CH_2)_nSiMe_{3-m}Cl_m$ wherein n is 0 to 2 and m is 0 to 3, aromatic groups, $Ar(R')_q$ wherein Ar is $C_{6-14}$ aromatic hydrocarbon, R' is a $C_{1-4}$ alkyl, halogen, alkoxy, or vinyl, and q is 0 to 5, a haloalkyl group, $(CH_2)_pX$ wherein p is 1 to 9 and X is a chloro or bromo; or an aromatic hydrocarbon, Ar $CH_2X$ wherein Ar is $C_{6-14}$ aromatic hydrocarbon and X is a chloro or bromo. in formula I, $R^3$ is the same as $R^2$ in formula III and further, $R^3$ can also be $(CH_2)_pSiR^1Cl_2$ or $ArCH_2SiR^1Cl_2$ when $R^2$ in formula III is $(CH_2)_pX$ or $ArCH_2X$, because of the coupling reaction of X with the compound of formula II.

DETAILED DESCRIPTION OF THE INVENTION

In a sealed stainless steel tube, hydrochlorosilane represented by formula II, organic halide of formula III, solvent, and catalyst are placed all together under inert atmosphere. The amount of hydrochlorosilane of formula II used is two times or more, preferably 2 to 5 folds, relative to the amount of the compounds of formula III. Lewis bases of tertiary amine or tertiary phosphine are used as a catalyst in an amount sufficient to catalyze the reaction, generally, about 0.01 to 0.4 moles of the catalyst per mole of the organic halide of formula III. The catalysts can be represented by the following formula IV:

wherein, Z is a nitrogen or phosphorus, each R" is independently selected from a $C_{1-12}$ alkyl, $C_{1-6}$ alkyl substituted aromatic, or phenyl group and two R" can be covalently bonded to each other to form a cyclic compound.

The catalyst can also be a transition metal compound having one or more $ZR"_3$ group wherein Z and R" are as defined above.

It is also possible to use the catalyst having the following formula V:

wherein, Z and R" are defined as above.

The catalyst can also be an aromatic amine such as pyridine, having 1 to 12 carbon atoms and 1 to 3 nitrogen atoms.

The above catalysts can be used in an immobilized form on a silicon resin, silica, inorganic supporter or organic polymer.

In the reaction, a co-catalyst such as CuCl or Cu can be used in addition to the above mentioned catalysts. The reaction can be carried out in most organic solvents such as toluene, hexane, tetrahydrofurane, or acetonitrile, but it also proceeds in neat condition. After sealing the reaction tube with a stainless steel stopper, heating and stirring may be carried out for a certain period of time, generally between 1 hour to about 48 hours, to complete the reaction. The reaction is carried out at a temperature from 10° C. to 250° C., but the preferred reaction temperature range is 130° C. to 200° C. After completion of the reaction, the products are distilled under atmospheric pressure or vacuum.

The invention will be further illustrated by the following examples. It is, however, not intended that this invention will be limited by the examples.

EXAMPLE 1

Reaction of 1-chlorohexane and trichlorosilane in the presence of tri-n-butylphosphine In a 25 ml oven dried stainless steel tube, 0.15 g (0.75 mmol) of tri-n-butylphosphine, 0.90 g (7.5 mmol) of 1-chlorohexane, and 5.08 g (37.5 mmol) of trichlorosilane were added under a dry nitrogen atmosphere. After sealing the cylinder with a valve, the reactor was maintained at 150° C. for 12 hrs. The resulting mixture was distilled to yield 1.1 g of n-hexyltrichlorosilane (bp; 215–219° C., yield; 65%).

n-Hexyltrichlorosilane; H-NMR (CDCl$_3$, ppm): 0.88–0.94 (m, 3H, —CH$_3$), 1.30–1.45 (m, 6H, (CH$_2$)$_4$), 1.52–1.63 (m, 2H, SiCH$_2$).

EXAMPLE 2

Reaction of 1-chlorohexane and dichlorosilane in the presence of tri-n-butylphosphine In the same apparatus and procedure as Example 1 above, 0.21 ml (0.86 mmol) of tri-n-butylphosphine, 1.18 ml (8.6 mmol) of 1-chlorohexane, and 4.3 g (43 mmol) of dichlorosilane were reacted at 150° C. for 12 hrs. The resulting mixture was distilled to give 0.93 g of n-hexyltrichlorosilane (yield; 33%) and n-hexyldichlorosilane (yield; 18%).

n-Hexyldichlorosilane; H-NMR(CDCl$_3$, ppm):0.88–0.94 (m, 3H, CH$_3$), 1.30–1.45 (m, 6H, (CH$_2$)$_4$), 1.49–1.60 (m, 2H, SiCH$_2$), 5.47 (t, J=1.8 Hz, 1H, SiH).

EXAMPLE 3

Reaction of 1-chlorohexane and methyldichlorosilane in the presence of tri-n-butylphosphine In the same apparatus and procedure as Example 1 above, 0.15 g (0.75 mmol) of tri-n-butylphosphine, 0.90 g (7.5 mmol) of 1-chlorohexane, and 3.90 ml (37.5 mmol) of methyldichlorosilane were reacted at 150° C. for 12 hrs. The resulting mixture was distilled to give 0.25 g of 2,2-dichloro-2-silaoctane (yield:16%).

2,2-Dichloro-2-silaoctane; H-NMR(CDCl3, ppm): 0.88–0.91 (m, 3H, CH$_3$), 0.94 (s, 3H, SiCH$_3$), 1.30–1.45 (m, 6H, (CH$_2$)$_4$), 1.45–1.60 (m, 2H, SiCH$_2$).

EXAMPLE 4

Reaction of 1-chloro-3,3,3-trifluoropropane and trichlorosilane in the presence of tri-n-butylphosphine In the same apparatus and procedure as Example 1 above, 0.15 g (0.75 mmol) of tri-n-butylphosphine, 1.33 g (10.0 mmol) of 1-chloro-3,3,3-trifluoropropane, and 6.77 g (50.0 mmol) of trichlorosilane were reacted at 150° C. for 15 hrs. The resulting mixture was distilled to give 2.1 g of (3,3,3-trifluoropropyl)trichlorosilane (bp; 114° C., yield; 90%).

(3,3,3-Trifluoropropyl)trichlorosilane; MS (70 eV EI) m/z (relative intensity):137(24), 135(71), 133(72), 98(11), 78(87), 77(100), 69(20), 63(21), 59(26), 51(11).

EXAMPLE 5

Reaction of (chloromethyl)trichlorosilane and trichlorosilane in the presence of triphenylphosphine In the same apparatus and procedure as Example 1 above, 0.20 g (0.75 mmol) of triphenylphosphine, 0.92 g (7.5 mmol) of (chloromethyl)trichlorosilane, and 5.08 g (37.5 mmol) of trichlorosilane were reacted at 150° C. for 42 hrs. The resulting mixture was distilled to give 1.1 g of 1,1,1,3,3,3-hexachloro-1,3-disilapropane (bp; 173–174° C., yield; 50%) and 0.3 g of 1,1,1,3,3-pentachloro-1,3-disilapropane (bp; 166–167° C., yield; 16%).

1,1,1,3,3,3-Hexachloro-1,3-disilapropane; H-NMR (CDCl$_3$, ppm):1.87 (s, SiCH$_2$Si)

1,1,1,3,3-Pentachloro-1,3-disilapropane; H-NMR (CDCl$_3$, ppm):1.64 (d, J=2.2 Hz, 2H, SiCH$_2$Si), 5.72 (t, J=2.2 Hz, 1H, SiH).

Reaction of (chloromethyl)methyldichlorosilane and trichlorosilane in the presence of triphenylphosphine In the same apparatus and procedure as Example 1 above, 0.20 g (0.75 mmol) of triphenylphosphine, 1.07 g (7.5 mmol) of (chloromethyl)methyldichlorosilane, and 5.08 g (37.5 mmol) of trichlorosilane were reacted at 150° C. for 24 hrs. The resulting mixture was distilled to give 1.0 g of 1,1,1,3,3-pentachloro-1,3-disilabutane (bp; 181–182° C., yield; 58%) and 0.1 g of 1,1,3,3-tetrachloro-1,3-disilabutane (bp; 166–167° C., yield; 14%).

1,1,1,3,3-Pentachloro-1,3-disilabutane; H-NMR (CDCl$_3$, ppm):0.94 (s, 3H, SiCH$_3$), 1.58 (s, SiCH$_2$Si)

1,1,3,3-Tetrachloro-1,3-disilabutane; H-NMR (CDCl$_3$, ppm):0.94 (s, 3H, SiCH$_3$), 1.34 (d, J=2.3 Hz, 2H, SiCH$_2$Si), 5.69 (t, J=2.3 Hz, 1H, SiH).

EXAMPLE 7

Reaction of (chloromethyl)methyldichlorosilane and trichlorosilane in the presence of triethylamine In the same apparatus and procedure as Example 1 above, 0.063 g (0.62 mmol) of triethylamine, 1.0g (6.2 mmol) of (chloromethyl)methyldichlorosilane, and 4.18 g (30.9 mmol) of trichlorosilane were reacted at 200° C. for 24 hrs. The resulting mixture was distilled to give 0.50 g of 1,1,1,3,3-pentachloro-1,3-disilabutane (yield; 31%).

EXAMPLE 8

Reaction of (chloromethyl)methyldichlorosilane and trichlorosilane in the presence of tri-n-butylamine In the same apparatus and procedure as Example 1 above, 0.115 g (0.62 mmol) of tri-n-butylamine, 1.0 g (6.2 mmol) of (chloromethyl)methyldichlorosilane, and 4.18 g (30.9 mmol) of trichlorosilane were reacted at 200° C. for 11 hrs. The resulting mixture was distilled to give 0.50 g of 1,1,1,3,3-pentachloro-1,3-disilabutane (yield; 6%).

EXAMPLE 9

Reaction of (chloromethyl)dimethylchlorosilane and trichlorosilane in the presence of triphenylphosphine In the same apparatus and procedure as Example 1 above, 1.0 g (3.8 mmol) of triphenylphosphine, 6.21 g (38.0 mmol) of (chloromethyl)dimethylchlorosilane, and 27.5 g (190.0 mmol) of trichlorosilane were reacted at 150° C. for 12 hrs. The resulting mixture was distilled to give 5.8 g of 1,1,1,3-tetrachloro-3-methyl-1,3-disilabutane (bp; 169–170° C., yield; 58%) and 1.2 g of 1,1,3-trichloro-3-methyl-1,3-disilabutane (bp; 153–155° C., yield; 8%).

1,1,1,3-Tetrachloro-3-methyl-1,3-disilabutane; H-NMR (CDCl$_3$, ppm):0.62 (s, 6H, SiCH$_3$), 1.28 (s, 2H, SiCH$_2$Si)

1,1,3-Trichloro-3-methyl-1,3-disilabutane; H-NMR (CDCl$_3$, ppm):0.58 (s, 6H, SiCH$_3$), 1.00 (d, J=2.3 Hz, 2H, SiCH$_2$Si), 5.65 (t, J=2.3 Hz, 1H, SiH).

EXAMPLE 10

Reaction of (chloromethyl)trimethylsilane and trichlorosilane in the presence of triphenylphosphine In the same apparatus and procedure as Example 1 above, 0.20 g (0.75 mmol) of triphenylphosphine, 1.38 g (7.5 mmol) of (chloromethyl)trimethylsilane, and 5.08 g (37.5 mmol) of trichlorosilane were reacted at 150° C. for 10 hrs. The resulting mixture was distilled to give 1.2 g of 1,1,1,-trichloro-3,3-dimethyl-1,3-disilabutane (bp; 173–174° C., yield; 70%) and 0.1 g of 1,1-dichloro-3,3-dimethyl-1,3-disilabutane (bp; 157–159° C., yield; 7%).

1,1,1-Trichloro-3,3-dimethyl-1,3-disilabutane; H-NMR (CDCl$_3$, ppm):0.25 (s, 9H, SiCH$_3$), 0.85 (s, 2H, SiCH$_2$Si).

1,1-Dichloro-3,3-dimethyl-1,3-disilabutane; H-NMR (CDCl$_3$, ppm):0.17 (s, 9H, SiCH$_3$), 0.59 (d, J=2.4 Hz, 2H, SiCH$_2$Si), 5.60 (t, J=2.4 Hz, 1H, SiH).

EXAMPLE 11

Reaction of (2-chloroethyl)trimethylsilane and trichlorosilane in the presence of tetrakis (triphenylphosphine)palladium(0)

In the same apparatus and procedure as Example 1 above, 0.46 g (0.40 mmol) of tetrakis(triphenylphosphine) palladium(0), 1.03 g (7.5 mmol) of (2-chloroethyl) trimethylsilane, and 5.08 g (37.5 mmol) of trichlorosilane were reacted at 150° C. for 12 hrs. The resulting mixture was distilled to give 1.06 g of [(2-trichlorosilyl)ethyl] trimethylsilane (bp; 236° C., yield; 60%).

[(2-Trichlorosilyl)ethyl]trimethylsilane; H-NMR (CDCl$_3$, ppm):0.02 (s, 9H, Si(CH$_3$)$_3$), 0.50 (m, 2H, CH$_2$SiMe$_3$), 1.54 (m, 2H, Cl$_3$SiCH$_2$).

EXAMPLE 12

Reaction of (3-chloropropyl)trimethylsilane and trichlorosilane in the presence of tri-n-butylphosphine In the same apparatus and procedure as Example 1 above, 0.15 g (0.75 mmol) of tri-n-butylphosphine, 1.61 g (7.5 mmol) of (3-chloropropyl)trimethylsilane, and 5.08 g (37.5 mmol) of trichlorosilane were reacted at 150° C. for 12 hrs. The resulting mixture was distilled to give 1.06 g of [(3-trichlorosilyl)propyl]trimethylsilane (bp; 250–258° C., yield; 86%).

[(3-trichlorosilyl)propyl]trimethylsilane; H-NMR (CDCl$_3$, ppm):0.02 (s, 9H, SiCH$_3$), 0.66 (m, 2H, Me$_3$SiCH$_2$), 1.47 (m, 2H, CH$_2$), 1.61 (m, 2H, CH$_2$SiCl$_3$)

EXAMPLE 13

Reaction of allyl chloride and trichlorosilane in the presence of triphenylphosphine In the same apparatus and procedure as Example 1 above, 0.037 g (0.14 mmol) of triphenylphosphine, 1.07 g (14.0 mmol) of allyl chloride, and 9.48 g (70.0 mmol) of trichlorosilane were reacted at 150° C. for 10 hrs. The resulting mixture was distilled to give 1.2 g of allyltrichlorosilane (bp; 117–8° C., yield; 49%), 0.12 g of propyltrichlorosilane (bp; 123–5° C., yield; 5%), and 0.24 g of (3-chloropropyl) trichlorosilane (bp; 181–2° C., yield; 8%).

Allyltrichlorosilane; H-NMR (CDCl$_3$, ppm):2.35–2.37 (d, 2H, CH$_2$), 5.18–5.24 (m, 2H,CH$_2$=), 5.71–5.85 (m, 1H, CH=).

(3-Chloropropyl)trichlorosilane; H-NMR (CDCl$_3$, ppm): 1.58 (m, 2H, SiCH$_2$), 2.06 (m, 2H, CH$_2$—), 3.61 (t, J=6.48, 2H, CH$_2$Cl).

EXAMPLE 14

Reaction of allyl chloride and trichlorosilane in the presence of bis(diphenylphosphino)methane In the same apparatus and procedure as Example 1 above, 0.305 g (0.794 mmol) of bis(diphenylphosphino)methane, 0.612 g (8.0 mmol) of allyl chloride, and 4.33 g (32 mmol) of trichlorosilane were reacted at 150° C. for 1 hr. The resulting mixture was distilled to give 0.73 g of allytrichlorosilane (yield; 52%).

EXAMPLE 15

Reaction of allyl chloride and trichlorosilane in the presence of 1,2-bis(diphenylphosphino)ethane In the same apparatus and procedure as Example 1 above, 0.290 g (0.729 mmol) of 1,2-bis(diphenylphosphino)ethane, 0.558 g (7.3 mmol) of ally chloride, and 3.96 g (29 mmol) of trichlorosilane were reacted at 150° C. for 1 hr. The resulting mixture was distilled to give 0.58 g of allytrichlorosilane (yield; 45%).

EXAMPLE 16

Reaction of allyl chloride and trichlorosilane in the presence of triphenylphosphine and CuCl In the same apparatus and procedure as Example 1 above, 0.037 g (0.14 mmol) of triphenylphosphine, 1.4 mg (0.014 mmol) of CuCl, 1.07 g (14.0 mmol) of allyl chloride, and 9.48 g (70.0 mmol) of trichlorosilane were reacted at 150° C. for 10 hrs. The resulting mixture was distilled to give 0.5 g of allytrichlorosilane (bp; 117–8° C., yield; 20%), 0.51 g of propyltrichlorosilane (bp; 123–5° C., yield; 20%), and 0.73 g of 1,3-bis(trichlorosilyl)propane (bp; 88–90° C./12.5 mmHg, yield; 17%).

EXAMPLE 17

Reaction of allyl chloride and trichlorosilane in the presence of triethylamine

In the same apparatus and procedure as Example 1 above, 0.077 g (0.76 mmol) of triethylamine, 0.60 g (7.6 mmol) of allyl chloride, and 5.10 g (37.7 mmol) of trichlorosilane were reacted at 150° C. for 8 hrs. The resulting mixture was distilled to give 0.29 g of allyltrichlorosilane (yield; 21%).

EXAMPLE 18

Reaction of allyl chloride and trichlorosilane in the presence of pyridine

In the same apparatus and procedure as Example 1 above, 0.12 g (1.52 mmol) of pyridine, 0.60 g (7.6 mmol) of allyl chloride, and 5.10 g (37.7 mmol) of trichlorosilane were reacted at 170° C. for 3 hrs. The resulting mixture was distilled to give 0.45 g of allyltrichlorosilane (yield; 34%).

EXAMPLE 19

Reaction of allyl chloride and trichlorosilane in the presence of immobolized tertiary amine catalyst In the same apparatus and procedure as Example 1 above, 0.60 g of tertiary amine containing silicon resin {[$RSiO_{3/2}]_n$, R=3-(N-pyrrolidino)propyl}, 0.60 g (7.6 mmol) of allyl chloride, and 5.09 g (37.6 mmol) of trichlorosilane were reacted at 150° C. for 6 hrs. The resulting mixture was distilled to give 0.53 g of allyltrichlorosilane (yield; 39%).

EXAMPLE 20

Reaction of allyl choride and methyldichlorosilane in the presence of triphenylphosphine In the same apparatus and procedure as Example 1 above, 0.34 g (1.4 mmol) of triphenylphosphine, 1.07 g (14.0 mmol) of allyl chloride, and 8.05 g (70.0 mmol) of methyldichlorosilane were reacted at 150° C. for 10 hrs. The resulting mixture was distilled to give 0.4 g of allylmethyldichlorosilane (bp; 119–120° C., yield; 20%) and 0.1 g of allylmethylchlorosilane (bp; 85–90° C., yield; 5%).

Allylmethyldichlorosilane; MS (70 eV EI) m/z (relative intensity):156(13), 154(18), 141(13), 139(20), 117(13), 115 (70), 114(9), 113(100), 65(7), 63(22).

EXAMPLE 21

Reaction of allyl chloride and dichlorosilane in the presence of triphenylphosphine In the same apparatus and procedure as Example 1 above, 0.80 g (3.1 mmol) of triphenylphosphine, 1.25 ml (15.3 mmol) of allyl chloride, and 3.1 g (31 mmol) of dichlorosilane were reacted 150° C. for 1.5 hrs. The resulting mixture was distilled to give 1.00 g of allyldichlorosilane (yield; 13%) and allyltrichlorosilane (yield; 20%).

Allyldichlorosilane; H-NMR ($CDCl_3$, ppm):2.17–2.19 (d, 2H, $SiCH_2$), 5.13–5.18 (m, 2H, $CH_2$=), 5.47 (t, J=1.8 Hz, 1H, SiH), 5.71–5.85 (m, 1H, CH=).

EXAMPLE 22

Reaction of allyl bromide and trichlorosilane in the presence of triphenylphosphine In the same apparatus and procedure as Example 1 above, 0.037 g (0.14 mmol) of triphenylphosphine, 1.69 g (14.0 mmol) of allyl bromide, and 9.48 g (70.0 mmol) of trichlorosilane were reacted at 150° C. for 2 hrs. The resulting mixture was distilled to give 2.37 g of allyltrichlorosilane (bp; 117–8° C., yield; 95%).

EXAMPLE 23

Reaction of allyl bromide and trichlorosilane in the presence of triethylamine

In the same apparatus and procedure as Example 1 above, 0.077 g (0.76 mmol) of triethylamine, 0.60 g (7.6 mmol) of allyl chloride, and 5.10 g (37.7 mmol) of trichlorosilane were reacted at 150° C. for 8 hrs. The resulting mixture was distilled to give 0.29 g of allyltrichlorosilane (yield; 21%).

EXAMPLE 24

Reaction of allyl bromide and trichlorosilane in the presence of N,N,N',N'-tetramethylethylenediamine In the same apparatus and procedure as Example 1 above, 0.058 g (0.5 mmol) of N,N,N',N'-tetramethylethylenediamine, 0.61 g (5.0 mmol) of allyl bromide, and 3.41 g (25.2 mmol) of trichlorosilane were reacted at 200° C. for 5 hrs. The resulting mixture was distilled to give 0.18 g of allyltrichlorosilane (yield; 13%).

EXAMPLE 25

Reaction of crotyl chloride and trichlorosilane in the presence of tri-n-butylphosphine In the same apparatus and procedure as Example 1 above, 0.061 g (0.30 mmol) of tri-n-butylphosphine, 0.272 g (14.9 mmol) of crotyl chloride, and 2.02 g (70.0 mmol) of trichlorosilane were reacted at 150° C. for 1.5 hrs. The resulting mixture was distilled to give 0.40 g of crotyltrichlorosilane (yield; 65%).

Crotyltrichlorosilane; MS (70 eV EI) m/z (relative intensity):190(7), 188(7), 135(10), 133(10), 63(7), 56(6), 55(100), 54(11), 53(8).

EXAMPLE 26

Reaction of crotyl chloride and trichlorosilane in the presence of tri-n-propylamine In the same apparatus and procedure as Example 1 above, 0.09 g (0.6 mmol) of tri-n-propylamine, 0.6 g (6.6 mmol) of crotyl chloride, and 4.49 g (33.1 mmol) of trichlorosilane were reacted at 150° C. for 6 hrs. The resulting mixture was distilled to give 0.68 g of crotyltrichlorosilane (yield; 65%).

EXAMPLE 27

Reaction of crotyl chloride and trichlorosilane in the presence of tri-n-butylamine In the same apparatus and procedure as Example 1 above, 0.12 g (0.6 mmol) of tri-n-butylamine, 0.6 g (6.6 mmol) of crotyl chloride, and 4.49 g (33.1 mmol) of trichlorosilane were reacted at 150° C. for 6 hrs. The resulting mixture was distilled to give 1.02 g of crotyltrichlorosilane (yield; 89%).

EXAMPLE 28

Reaction of crotyl chloride and trichlorosilane in the presence of N,N,N',N'-tetramethylethylenediamine In the same apparatus and procedure as Example 1 above, 0.11 g (0.6 mmol) of N,N,N',N'-tetramethylethylenediamine, 0.6 g (6.6 mmol) of crotyl chloride, and 4.49 g (33.1 mmol) of trichlorosilane were reacted at 150° C. for 6 hrs. The resulting mixture was distilled to give 0.45 g of crotyltrichlorosilane (yield; 39%).

EXAMPLE 29

Reaction of crotyl chloride and trichlorosilane in the presence of pyridine and CuCl In the same apparatus and procedure as Example 1 above, 0.1 g (1.2 mmol) of pyridine, 0.02 g (0.2 mmol) of CuCl, 0.6 g (6.6 mmol) of crotyl chloride, and 4.49 g (33.1 mmol) of trichlorosilane were reacted at 200° C. for 15 hrs. The resulting mixture was distilled to give 0.99 g of crotyl-trichlorosilane (yield; 79%).

EXAMPLE 30

Reaction of benzyl chloride and trichlorosilane in the presence of tri-n-butylphosphine In the same apparatus and procedure as Example 1 above, 0.15 g (0.75 mmol) of tri-n-butylphosphine, 0.95 g (7.5 mmol) of benzyl chloride, and 5.08 g (37.5 mmol) of trichlorosilane were reacted at 150° C. for 2 hrs. The resulting mixture was distilled to give 1.6 g of benzyltrichlorosilane (bp; 140–2° C./10 mmHg, yield; 96%).

Benzyltrichlorosilane; H-NMR (CDCl$_3$, ppm):2.92 (s, 2H, CH$_2$), 7.29–7.36 (m, 5H, ArH).

EXAMPLE 31

Reaction of benzyl chloride and trichlorosilane in the presence of triethylamine In the same apparatus and procedure as Example 1 above, 0.051 g (0.5 mmol) of triethylamine, 0.63 g (5.0 mmol) of benzyl chloride, and 3.41 g (25.2 mmol) of trichlorosilane were reacted at 150° C. for 18 hrs. The resulting mixture was distilled to give 0.52 g of benzyltrichlorosilane (yield; 47%).

EXAMPLE 32

Reaction of benzyl chloride and trichlorosilane in the presence of tri-n-butylamine In the same apparatus and procedure as Example 1 above, 0.090 g (0.5 mmol) of tri-n-butylamine, 0.63 g (5.0 mmol) of benzyl chloride, and 3.41 g (25.2 mmol) of trichlorosilane were reacted at 150° C. for 6 hrs. The resulting mixture was distilled to give 0.32 g of benzyltrichlorosilane (yield; 29%).

EXAMPLE 33

Reaction of benzyl chloride and trichlorosilane in the presence of N,N,N',N'-tetramethylethylenediamine In the same apparatus and procedure as Example 1 above, 0.116 g (1.0 mmol) of N,N,N',N'-tetramethylethylenediamine, 0.63 g (5.0 mmol) of benzyl chloride, and 3.41 g (25.2 mmol) of trichlorosilane were reacted at 200° C. for 7 hrs. The resulting mixture was distilled to give 0.57 g of benzyltrichlorosilane (yield; 52%).

EXAMPLE 34

Reaction of benzyl chloride and trichlorosilane in the presence of pyridine

In the same apparatus and procedure as Example 1 above, 0.08 g (1.0 mmol) of pyridine, 0.63 g (5.0 mmol) of benzyl chloride, and 3.41 g (25.2 mmol) of trichlorosilane were reacted at 200° C. for 6 hrs. The resulting mixture was distilled to give 0.12 g of benzyltrichlorosilane (yield; 11%).

EXAMPLE 35

Reaction of benzyl chloride and methyldichlorosilane in the presence of tri-n-butylphosphine In the same apparatus and procedure as Example 1 above, 0.15 g (0.75 mmol) of tri-n-butylphosphine, 0.95 g (7.5 mmol) of benzyl chloride, and 4.31 g (37.5 mmol) of methyldichlorosilane were reacted at 200° C. for 2 hrs. The resulting mixture was distilled to give 0.31 g of benzylmethyldichlorosilane (bp; 214–215° C./740 mmHg, yield; 20%).

Benzylmethyldichlorosilane; H-NMR (CDCl$_3$, ppm):0.96 (s, 3H, SiCH$_3$), 2.85 (s, 2H, CH$_2$), 7.29–7.36 (m, 5H, ArH).

EXAMPLE 36

Reaction of benzyl chloride and dichlorosilane in the presence of tri-n-butylphosphine In the same apparatus and procedure as Example 1 above, 0.21 ml (0.984 mmol) of tri-n-butylphosphine, 0.97 ml (8.4 mmol) of benzyl chloride, and 1.7 g (16.8 mmol) of dichlorosilane were reacted at 150° C. for 3 hrs. The resulting mixture was distilled to give 1.51 g of benzyldichlorosilane (yield; 23%) and benzyltrichlorosilane (yield; 60%).

Benzyldichlorosilane; H-NMR (CDCl$_3$, ppm):2.76 (s, J=2.0 Hz, 2H, CH$_2$), 5.54 (t, J=2.0 Hz, 1H, SiH), 7.18–7.37 (m, 5H, ArH).

EXAMPLE 37

Reaction of 4-fluorobenzyl chloride and trichlorosilane in the presence of tri-n-bytylphosphine In the same apparatus and procedure as Example 1 above, 0.15 g (0.75 mmol) of tri-n-butylphosphine, 1.08 g (7.5 mmol) of 4-fluorobenzyl chloride, and 5.08 g (37.5 mmol) of trichlorosilane were reacted at 150° C. for 2 hrs. The resulting mixture was distilled to give 1.6 g of (4-fluorobenzyl)trichlorosilane (bp; 56° C./13 mmHg, yield; 96%).

(4-Fluorobenzyl)trichlorosilane; H-NMR (CDCl$_3$, ppm): 2.89 (s, 2H, —CH$_2$—), 7.00–7.20 (m, 4H, ArH).

EXAMPLE 38

Reaction of 4-fluorobenzyl chloride and trichlorosilane in the presence of triethylamine In the same apparatus and procedure as Example 1 above, 0.044 g (0.40 mmol) of triethylamine, 0.60 g (4.0 mmol) of 4-fluorobenzyl chloride, and 2.71 g (20.0 mmol) of trichlorosilane were reacted at 150° C. for 40 hrs. The resulting mixture was distilled to give 0.24 g of (4-fluorobenzyl) trichlorosilane (yield; 24%).

EXAMPLE 39

Reaction of 4-chlorobenzyl chloride and trichlorosilane in the presence of tri-n-butylphosphine In the same apparatus and procedure as Example 1 above, 0.15 g (0.75 mmol) of tri-n-butylphosphine, 1.21 g (7.5 mmol) of 4-chlorobenzyl chloride, and 5.08 g (37.5 mmol) of trichlorosilane were reacted at 150° C. for 2 hrs. The resulting mixture was distilled to give 1.8 g of (4-Chlorobenzyl)trichlorosilane; H-NMR (CDCl$_3$, ppm): 2.93 (s, 2H, —CH$_2$—), 7.29–7.38 (m, 4H, ArH).

EXAMPLE 40

Reaction of 4-methoxybenzyl chloride and trichlorosilane in the presence of triphenylphosphine In the same apparatus and procedure as Example 1 above, 0.056 g (0.2 mmol) of tricyclohexylphosphine, 0.271 ml (2.0 mmol) of 4-methoxybenzyl chloride, and 1.00 ml (9.91 mmol) of trichlorosilane were reacted at 150° C. for 2 hrs. The resulting mixture was distilled to give 0.23 g of (4-methoxybenzyl)trichlorosilane (yield; 47%).

(4-Methoxybenzyl)trichlorosilane; MS(70 eV EI) m/z (relative intensity):256(7), 254(7), 135(5), 133(5), 122(9), 121(100), 78(10), 77(8).

EXAMPLE 41

Reaction of 4-methoxybenzyl chloride and trichlorosilane in the presence of N,N-dimethyltoluidine In the same apparatus and procedure as Example 1 above, 0.06 g (0.45 mmol) of N,N-dimethyltoluidine, 0.7 g (4.5 mmol) of 4-methoxybenzyl chloride, and 3.05 g (22.5 mmol) of trichlorosilane were reacted at 200+ C. for 15 hrs. The resulting mixture was distilled to give 0.13 g of (4-methoxybenzyl)trichlorosilane (yield; 11%).

EXAMPLE 42

Reaction of 4-phenylbenzyl chloride and trichlorosilane in the presence of tri-n-butylphosphine In the same apparatus and procedure as Example 1 above, 0.15 g (0.75 mmol) of tri-n-butylphosphine, 1.52 g (7.5 mmol) of 4-phenylbenzyl chloride, and 5.08 g (37.5 mmol) of trichlorosilane were reacted at 150° C. for 2 hrs. The resulting mixture was distilled to give 2.0 g of (4-phenylbenzyl)trichlorosilane (mp; 60–65° C., yield; 90%).

(4-Phenylbenzyl)trichlorosilane; H-NMR (CDCl$_3$, ppm): 2.90 (s, 2H, CH$_2$), 7.20–7.40 (m, 9H, ArH).

EXAMPLE 43

Reaction of dichloromethane and trichlorosilane in the presence of tri-n-butylphosphine In the same apparatus and procedure as Example 1 above, 0.30 g (1.5 mmol) of tri-n-butylphosphine, 0.64 g (7.5 mmol) of dichloromethane, and 10.2 g (75.0 mmol) of trichlorosilane were reacted at 150° C. for 6 hrs. The resulting mixture was distilled to give a small amount of bis(trichlorosilyl)methane.

Bis(trichlorosilyl)methane; H-NMR (CDCl$_3$, ppm):1.59 (s, SiCH$_2$).

EXAMPLE 44

Reaction of 1,2-dichloroethane and trichlorosilane in the presence of tri-n-butylphosphine In the same apparatus and procedure as Example 1 above, 0.30 g (1.5 mmol) of tri-n-butylphosphine, 0.74 g (7.5 mmol) of 1,2-dichloroethane, and 10.2 g (75.0 mmol) of trichlorosilane were reacted at 150° C. for 12 hrs. The resulting mixture was distilled to give 1.5 g of 1,2-bis (trichlorosilyl)ethane (bp; 201° C., yield; 67%) and 0.1 g of 2-(chloroethyl)trichlorosilane (bp; 152–3° C., yield; 5%).

1,2-Bis-(trichlorosilyl)ethane; H-NMR (CDCl$_3$, ppm): 1.59 (s, 4H, SiCH$_2$).

EXAMPLE 45

Reaction of 1,3-dichloropropane and trichlorosilane in the presence of tri-n-butylphosphine In the same apparatus and procedure as Example 1 above, 0.30 g (1.5 mmol) of tri-n-butylphosphine, 0.85 g (7.5 mmol) of 1,3-dichloropropane, and 10.2 g (75.0 mmol) of trichlorosilane were reacted at 150° C. for 12 hrs. The resulting mixture was distilled to give 1.6 g of 1,3-bis (trichlorosilyl)propane (bp; 104° C./12.5 mmHg, yield; 70%) and 0.3 g of 3-(chloropropyl)trichlorosilane (bp; 88–90° C./12.5 mmHg, yield; 20%).

1,3-Bis(trichlorosilyl)propane; H-NMR (CDCl$_3$, ppm): 1.56 (m, 4H, SiCH$_2$), 1.92 (m, 2H, CH$_2$).

3-(Chloropropyl)trichlorosilane; H-NMR (CDCl$_3$, ppm): 1.58 (m, 2H, SiCH$_2$), 2.06 (m, 2H, CH$_2$), 3.61 (t, J=6,48, 2H, CH$_2$Cl).

EXAMPLE 46

Reaction of 1,3-dichloropropane and trichlorosilane in the presence of triethylamine In the same apparatus and procedure as Example 1 above, 0.048 g (0.47 mmol) of triethylamine, 0.6 g (4.7 mmol) of 1,3-dichloropropane, and 3.18 g (23.5 mmol) of trichlorosilane were reacted at 200° C. for 15 hrs. The resulting mixture was distilled to give 0.13 g of 1,3-bis(trichlorosilyl) propane (yield; 9%).

EXAMPLE 47

Reaction of 1-bromo-3-chloropropane and trichlorosilane in the presence of tri-n-butylphosphine In the same apparatus and procedure as Example 1 above, 0.30 g (1.5 mmol) of tri-n-butylphosphine, 1.18 g (7.5 mmol) of 1-bromo-3-chloropropane, and 10.2 g (75.0 mmol) of trichlorosilane were reacted at 150° C. for 18 hrs. The resulting mixture was distilled to give 1.1 g of 1,3-bis (trichlorosily)propane (bp; 104° C./12.5 mmHg, yield; 48%), 0.3 g of 3-bromopropyl)trichlorosilane (yield; 21%), and 0.2 g of 3-(chloropropyl)trichlorosilane (bp; 88–90° C./12.5 mmHg, yield; 11%).

EXAMPLE 48

Reaction of 1,4-dichlorobutane and trichlorosilane in the presence of tri-n-butylphosphine In the same apparatus and procedure as Example 1 above, 0.30 g (1.5 mmol) of tri-n-butylphosphine, 0.96 g (7.5 mmol) of 1,4-dichlorobutane, and 10.2 g (75.0 mmol) of trichlorosilane were reacted at 150° C. for 24 hrs. The resulting mixture was distilled to give 2.0 g of 1,4-bis (trichlorosilyl)butane (bp; 104° C./12.5 mmHg, yield; 84%).

1.4-Bis(trichlorosilyl)butane; H-NMR (CDCl$_3$, ppm): 1.46 (m, 4H, SiCH$_2$), 1.73 (m, 4H, CH$_2$).

EXAMPLE 49

Reaction of 1,4-bis(chloromethyl)benzene and trichlorosilane in the presence of tri-n-butylphosphine In the same apparatus and procedure as Example 1 above, 0.040 g (0.2 mmol) of tri-n-butylphosphine, 0.35 g (2.0 mmol) of 1,4-bis(chloromethyl)benzene, 1.34 g (9.91 mmol) of trichlorosilane, and 10 ml of dried benzene were reacted at 150° C. for 1.5 hrs. The resulting mixture was distilled to give 0.19 g of 1-chloromethyl-4-(trichlorosilylmethyl) benzene (yield; 34%) and 0.21 g of 1,4-bis (trichlorosilylmethyl)benzene (yield; 28%).

1-Chloromethyl-4-(trichlorosilylmethyl)benzene; MS (70 eV EI) m/z (relative intensity):274(23), 272(17), 241(37), 239(99), 238(17), 237(100), 139(33), 104(39), 103(32), 77(20).

1,4-Bis(trichlorosilylmethyl)benzene; MS (70 eV EI) m/z (relative intensity):372(15), 241(38), 240(16), 239(99), 238 (17), 237(100), 134(13), 132(14), 104(27), 103(19).

EXAMPLE 50

Reaction of 1,2-bis(chloromethyl)benzene and dichlorosilane in the presence of triphenylphosphine In the same apparatus and procedure as Example 1 above, 0.73 g (2.8 mmol) of triphenylphosphine, 4.9 g (28 mmol) of 1,2-bis(chloromethyl)benzene, 1.7 g (17 mmol) of dichlorosilane, and 10 ml of dried benzene were reacted at 150° C. for 3 hrs. The resulting mixture was distilled to give 2.33 g of 1-chloromethyl-2-(trichlorosilylmethyl)benzene (yield; 50%).

1-Chloromethyl-2-(trichlorosilymethyl)benzene; MS (70 eV EI) m/z (relative intensity):274(28), 272(22), 241(37), 239(100), 237(100), 139(57), 104(50), 103(54), 78(24), 77(33).

Having now fully described the present invention, it will be apparent to one of ordinary skill in the art that many changes and modifications can be made thereto without departing from the spirit of scope of the invention as set forth herein.

What is claimed is:

1. A process for preparing an organosilicon compound represented by formula I comprising: reacting a hydrochlorosilane represented by formula II with an organic halide represented by formula III in the presence of a Lewis base as a catalyst by a dehydrohalogenative coupling reaction;

$$R^3CH_2SiR^1Cl_2 \qquad (I)$$

$$HSiR^1Cl_2 \qquad (II)$$

$$R_2CH_2X \qquad (III)$$

wherein in formulas I and II, $R_1$ represents a hydrogen, chloro, or methyl; in formula III, X represents a chloro or bromo; in formula III, $R_2$ is selected from the group consisting of a $C_{1-17}$ alkyl, a $C_{1-10}$ fluorinated alkyl with partial or full fluorination, a $C_{1-5}$ alkenyl group, a silyl group silyl group containing alkyls $(CH_2)_nSiME_{3-m}Cl_m$ wherein n is 0 to 2 and m is 0 to 3, aromatic groups, $Ar(R')_1$ wherein Ar is $C_{6-14}$ aromatic hydrocarbon, R' is a $C_{1-4}$ alkyl, halogen, alkoxy, or vinyl, and q is 0 to 5, a haloalkyl group, $(CH_2)_pX$ wherein p is 1 to 9 and X is a chloro or bromo, an aromatic hydrocarbon, and $ArCH_2X$ wherein Ar is $C_{6-14}$ aromatic hydrocarbon and X is a chloro or bromo and further wherein in formula I, $R^3$ is the same as $R^2$ in formula III and further, $R^3$ can also be $(CH_2)_pSiR^1Cl_2$ when $R^2$ in formula III is $(CH_2)_pX$ or $ArCH_2X$.

2. A process according to claim 1, wherein the catalyst has the following formula IV:

$$ZR''_3 \qquad (IV)$$

wherein Z is a nitrogen or phosphorus, each R" is independently selected from a $C_{1-12}$ alkyl, $C_{1-6}$ alkyl substituted aromatic, or phenyl group and two R" can be covalently bonded to each other to form a cyclic compound.

3. A process according to claim 1, wherein the catalyst is a transition metal compound which have one or more $ZR''_3$ group as represented by formula IV as a ligand, $$ZR''_3 \qquad (IV)$$

wherein Z is a nitrogen or phosphorus, each R" is independently selected from a $C_{1-12}$ alkyl, $C_{1-6}$ alkyl substituted aromatic, or phenyl group and two R" can be covalently bonded to each other to form a cyclic compound.

4. A process according to claim 1, wherein the catalyst has the following general formula (V):

$$R''_2Z(CH_2)_yZR''_2 \qquad (V)$$

wherein $R''_2Z(CH_2)_yZR''_2$, Z is a nitrogen or phosphorus, each R" is independently selected from a $C_{1-12}$ alkyl, $C_{1-6}$ alkyl substituted aromatic, or phenyl group and two R" can be covalently bonded each other to form a cyclic compound.

5. A process according to claim 1, wherein the catalyst is an aromatic amine having 1 to 12 carbon atoms and 1 to 3 nitrogen atoms.

6. A process according to claim 1, wherein the catalyst has a tertiary amine or tertiary phosphine group immobilized on a silicon resin, silica, inorganic supporter or organic polymer.

7. A process according to claim 1, wherein a co-catalyst is further used.

8. A process according to claim 1, wherein an amount of catalyst used is 5–30% by mole of the compound of formula III.

9. A process according to claim 1, wherein the reaction temperature is 130–200° C.

10. A process according to claim 1, wherein an amount of the hydrochlorosilane of formula II used is two times or more than an amount of the organic halides of formula III.

11. A process according to claim 1, wherein the reaction is carried out in an organic solvent selected from the group consisting of toluene hexane, tetrahydrofuran, and acetonitrile.

12. A process according to claim 1, wherein the reaction is carried out in neat condition.

13. A process according to claim 5, wherein the catalyst is pyridine.

14. A process according to claim 7, wherein the co-catalyst is CuCl or Cu.

15. A process according to claim 8, wherein the amount of catalyst used is 10–20% by mole of the compound of formula III.

16. A process according to claim 9, wherein the reaction temperature is 150° C.

17. A process according to claim 10, wherein the amount of the hydrochlorosilane of formula II used is 2–5 fold of an amount of the organic halides of formula III.

* * * * *